(12) United States Patent
Meyer et al.

(10) Patent No.: US 6,263,914 B1
(45) Date of Patent: Jul. 24, 2001

(54) GAS DENSITY MONITOR ASSEMBLY

(75) Inventors: Jeffry R. Meyer, Greensburg; Willie B. Freeman, Irwin, both of PA (US)

(73) Assignee: ABB Power T&D Company Inc., Raleigh, NC (US)

(*) Notice: Subject to any disclaimer, the term of this patent is extended or adjusted under 35 U.S.C. 154(b) by 0 days.

(21) Appl. No.: 09/288,678

(22) Filed: Apr. 9, 1999

(51) Int. Cl.[7] .................................................. F16K 37/00
(52) U.S. Cl. ......................... 137/552; 137/377; 137/382; 137/557; 73/30.02; 73/438
(58) Field of Search ................................. 137/551, 557, 137/377, 382, 552; 73/30.02, 438

(56) References Cited

U.S. PATENT DOCUMENTS

| | | | |
|---|---|---|---|
| 3,063,287 | * 11/1962 | Hubbard | 73/30.02 |
| 3,365,932 | * 1/1968 | Greene, Jr. | 73/30.02 |
| 4,106,350 | 8/1978 | Morris et al. | 73/755 |
| 4,279,142 | 7/1981 | McIntyre | 73/1 G |
| 4,476,706 | 10/1984 | Hadden et al. | 73/1 G |
| 4,590,789 | 5/1986 | Kunze | 73/1 G |
| 5,143,114 | * 9/1992 | Daniels | 137/385 |
| 5,177,468 | * 1/1993 | Baldwin et al. | 137/551 |
| 5,388,451 | 2/1995 | Stendin et al. | 73/438 |
| 5,520,207 | * 5/1996 | Newsome et al. | 137/15 |
| 5,629,471 | 5/1997 | King | 73/1.01 |
| 5,665,894 | 9/1997 | Baker | 73/1.05 |
| 5,693,873 | 12/1997 | Thuries et al. | 73/23.28 |

* cited by examiner

Primary Examiner—A. Michael Chambers
(74) Attorney, Agent, or Firm—Woodcock Washburn Kurtz Mackiewicz & Norris LLP

(57) ABSTRACT

A density monitoring assembly for use in monitoring the gas density within a high voltage circuit breaker tank is disclosed. The density monitoring assembly is coupled directly to an exterior surface of said tank and provides electrical signals indicative of the density of gas within the tank. The assembly comprises a cover that encloses the density monitoring device. The device itself is used to retain the cover. A ball valve and a shraeder type valve are provided to allow testing of the device.

20 Claims, 8 Drawing Sheets

Section C-C

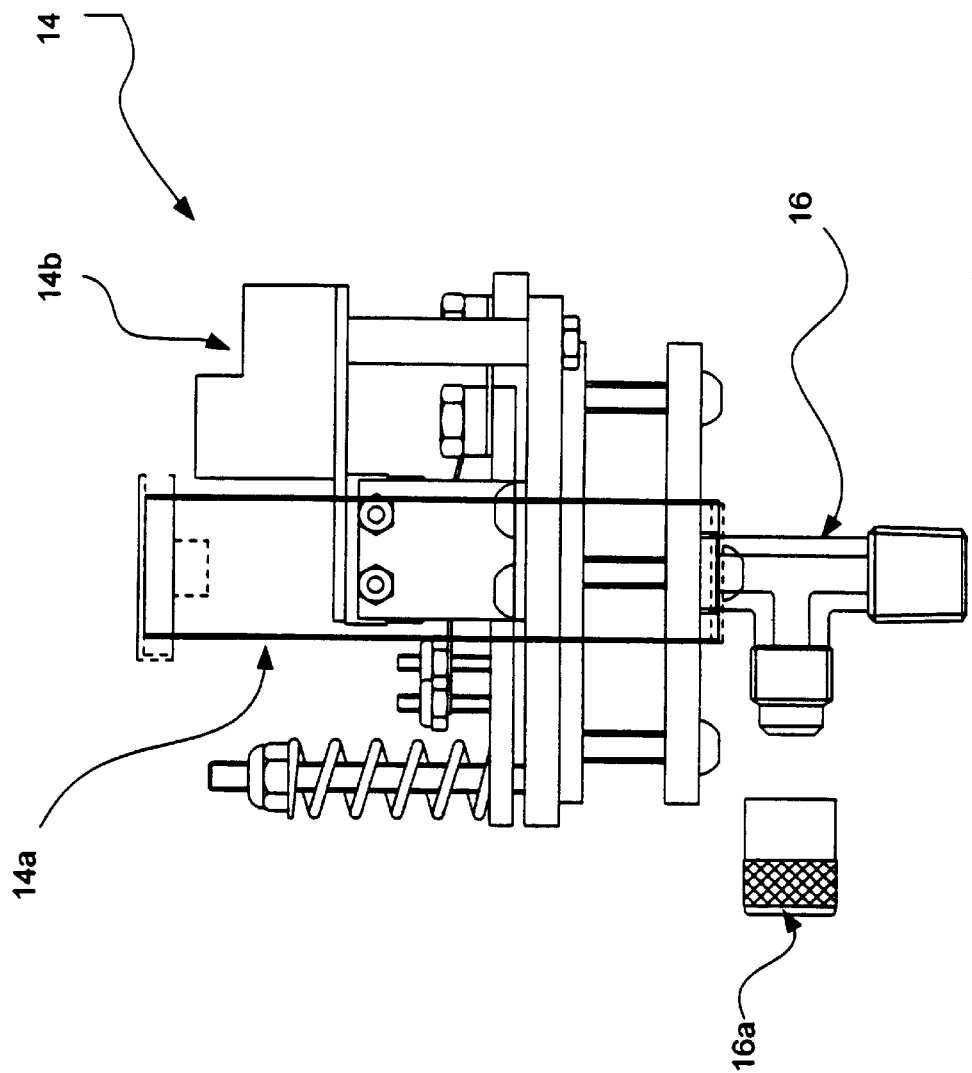

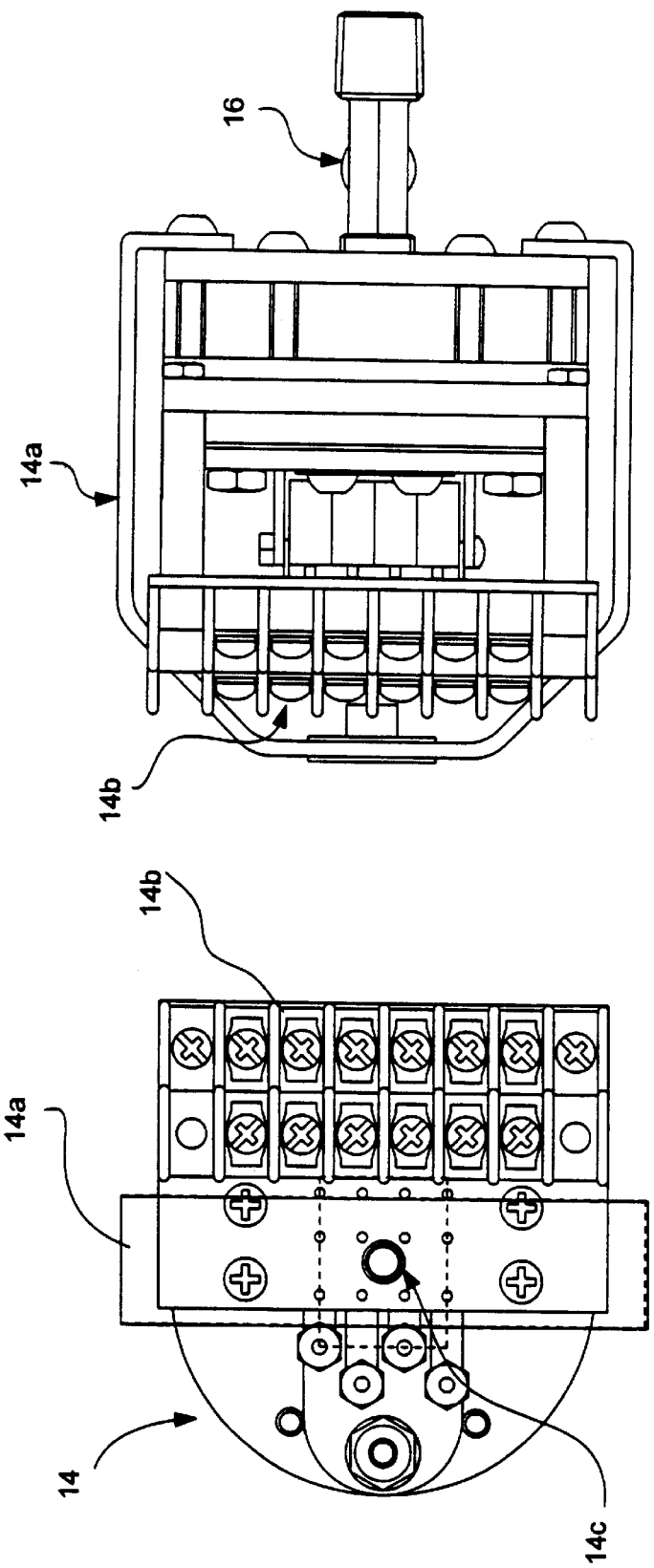

GAS DENSITY MONITOR ASSEMBLY

FIELD OF THE INVENTION

The present invention relates generally to gas monitors for containers of electrical switching gear. More particularly, the present invention relates to an assembly for attaching a gas density monitor to a tank containing an electrical switching component.

BACKGROUND OF THE INVENTION

A preferred application for the present invention is in tanks or vessels containing high voltage circuit breakers. Therefore, the background of the invention is described below in connection with such devices. However, it should be noted that, except where they are expressly so limited, the claims at the end of this specification are not intended to be limited to applications of the invention in a high voltage circuit breaker. For example, the invention disclosed herein may be employed in association with a circuit switcher, circuit breaker, load break switch, recloser, or the like.

A high voltage circuit breaker is a device used in the transmission and distribution of three phase electrical energy. When a sensor or protective relay detects a fault or other system disturbance on the protected circuit, the circuit breaker operates to physically separate current-carrying contacts in each of the three phases by opening the circuit to prevent the continued flow of current. In addition to its primary function of fault current interruption, a circuit breaker is capable of load current switching. A circuit switcher and a load break switch are other types of switching device. As used herein, the expression "switching device" encompasses circuit breakers, circuit switches, load break switches, reclosers, and any other type of electrical switch.

The major components of a circuit breaker or recloser include the interrupters, which function to open and close one or more sets of current carrying contacts housed therein; the operating mechanism, which provides the energy necessary to open or close the contacts; the arcing control mechanism and interrupting media, which interrupt current and create an open condition in the protected circuit; one or more tanks for housing the interrupters; and the bushings, which carry the high voltage electrical energy from the protected circuit into and out of the tank(s) (in a dead tank breaker). In addition, a mechanical linkage connects the interrupters and the operating mechanism.

Circuit breakers can differ in the overall configuration. However, the operation of most circuit breakers is substantially the same. For example, a circuit breaker may include a single tank assembly which houses all of the interrupters. U.S. Pat. No. 4,442,329, Apr. 10, 1984, "Dead Tank Housing for High Voltage Circuit Breaker Employing Puffer Interrupters," discloses an example of the single tank configuration. Alternatively, a separate tank for each interrupter may be provided in a multiple tank configuration. An example of a multiple tank circuit breaker is depicted in FIGS. 1A and 1B.

As shown in FIGS. 1A and 1B, the circuit breaker assembly 1 includes three cylindrical tanks 3. The three cylindrical tanks 3 form a common tank assembly 4 which is preferably filled with an inert, electrically insulating gas such as $SF_6$. The tank assembly 4 is referred to as a "dead tank" because it is at ground potential. Each tank 3 houses an interrupter (not shown). The interrupters are provided with terminals which are connected to respective spaced bushing insulators. The bushing insulators are shown as bushing insulators 5a and 6a for the first phase; 5b and 6b for the second phase; and 5c and 6c for the third phase. Associated with each pole or phase is a current transformer 7. In high voltage circuit breakers, the pairs of bushings for each phase are often mounted so that their ends have a greater spacing than their bases to avoid breakdown between the exposed conductive ends of the bushings. Such spacing may not be required in lower voltage applications. The operating mechanism that provides the necessary operating forces for opening and closing the interrupter contacts is contained within an operating mechanism housing 9. The operating mechanism is mechanically coupled to each of the interrupters via a linkage 8.

During circuit breaker opening or closure, a high voltage potential develops across the contacts. As a result, an electrical arc can develop across the switch contacts, particularly the closer the contacts are to closure. It is desirable to minimize this arc. For this and other reasons, such circuit breakers are housed in tanks 3 which are then be filled with an inert gas such as $SF_6$, which acts as an insulator to prevent arcing.

In order to ensure that the gas will perform its insulating task as design, it is important that the gas within the tank is maintained at about a preselected density. However, tanks may have leaks that over time allow the inert gas to escape from the tank. Hence, the density of the gas must be constantly monitored.

FIGS. 1A and 1B illustrate a prior art gas monitoring system. As illustrated in those Figures, a network of pipes 2 feeds the gas from each of the three tanks back to a single density monitoring device. As one might expect, if the density falls to an insufficient level, this design makes it difficult to determine the location, i.e., which tank is actually experiencing the leak and exposes all of the circuit breakers to failure from a leak in a single tank. Moreover, the intricate piping network also creates more places for leaks to occur.

The system of FIGS. 1A and 1B also includes a separate tank temperature monitor 15. The gas pressure and tank temperature are then fed into a control panel that calculates gas density.

Thus, there is a need for an improved gas density monitoring apparatus.

SUMMARY OF THE INVENTION

The invention meets the above need by providing an assembly for monitoring the fluidic contents of a tank containing an electrical circuit. Particularly, the system monitors a gas density of a tank containing a electrical circuit breaker in a inert gas filled tank. The assembly comprises a monitoring device in fluidic communication with the contents of the tank. The monitoring device is fixedly coupled at one end to an outside wall of the tank. A monitor device cover is disposed over the monitor device and against an outside wall of the tank to maintain the monitoring device at approximately the temperature of the tank.

The assembly is preferably fixed to the tank by way of the monitoring device. An insulator may be attached to an inside surface of the monitor device cover to maintain a temperature within said cover in relation to a temperature of the tank. Preferably, the assembly comprises a valve disposed between the monitoring device and the vessel.

Additionally, the invention contemplates the use of two different valve types. Preferably, at least one of the valves is a shut-off valve such as a ball valve. The other valve type is preferably a gas flow access valve, such as a shraeder valve. The shut-off valve is useful to shut-off the gas flow to the monitoring device during testing of the monitoring device.

Preferably, the shut-off valve handle is configured to prevent the cover from being placed back on the monitoring device when the valve is closed (i.e., shut-off). In this way, the invention insures that a valve that was shut-off during testing is not inadvertently left shut-off when testing is complete.

In addition, the invention contemplates the use of a shraeder valve between the shut-off valve and the monitoring device. A shraeder valve is similar to a tire valve, except of higher quality and having a metal body. An O-ring sealed cap is also employed to prevent leakage. The use of a shraeder valve provides a test point to apply a predetermined pressure to the monitoring device. Preferably, the monitoring device monitors density. More preferably, the monitoring device monitor pressure and temperature as a proxy for gas density.

The assembly further comprises a gasket disposed between the cover and the tank. The gasket preferably comprises a low temperature vinyl.

Other features and advantages of the present invention are disclosed below.

BRIEF DESCRIPTION OF THE DRAWINGS

FIGS. 5–7 illustrates side, top, and front plan views, respectively, of a gas density monitoring device employed in the gas density monitoring assembly;

DETAILED DESCRIPTION OF PREFERRED EMBODIMENTS

Figure 1A:
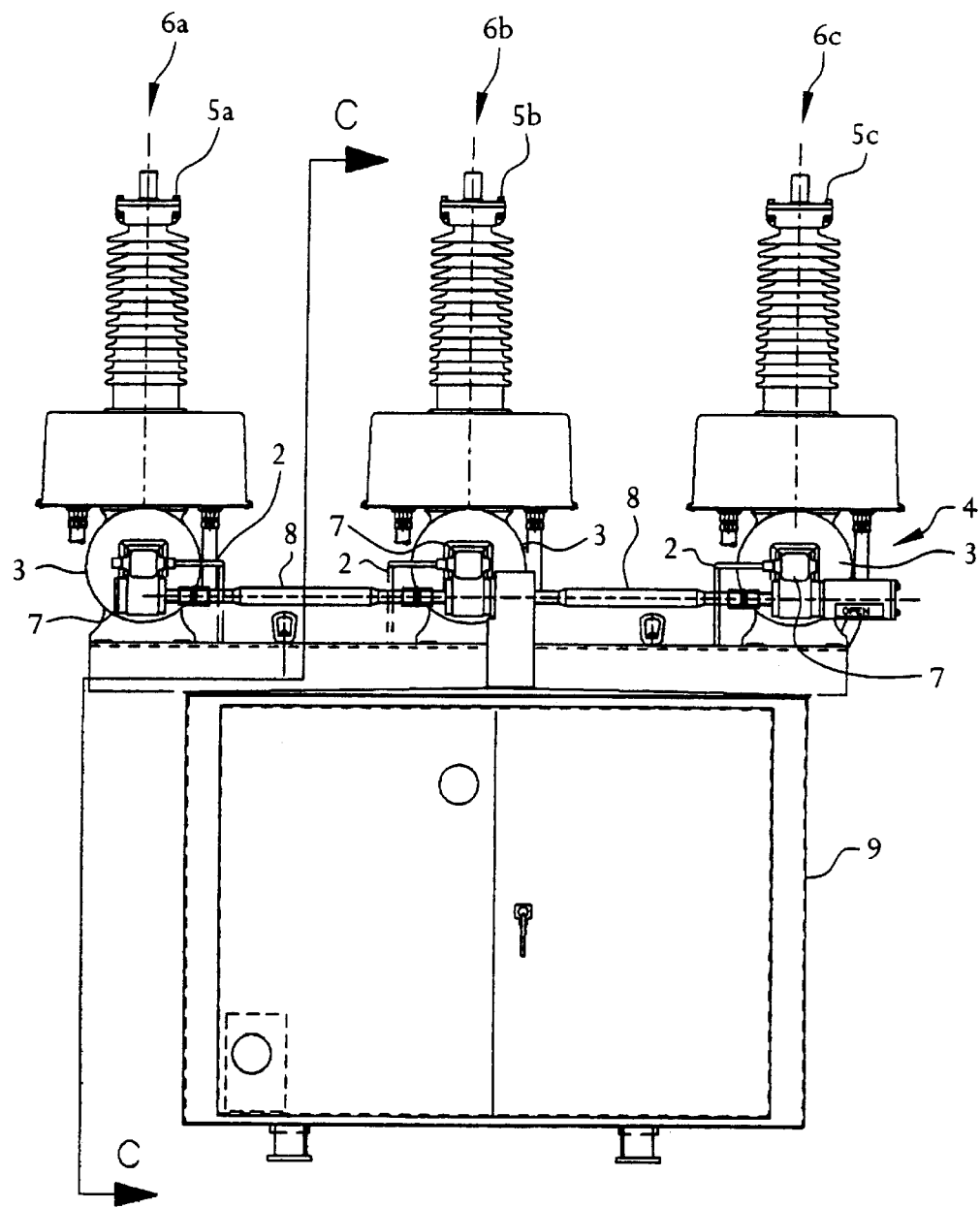
FIG. 1A is a front plan view of a multiple tank high voltage circuit breaker.
Figure 1B:
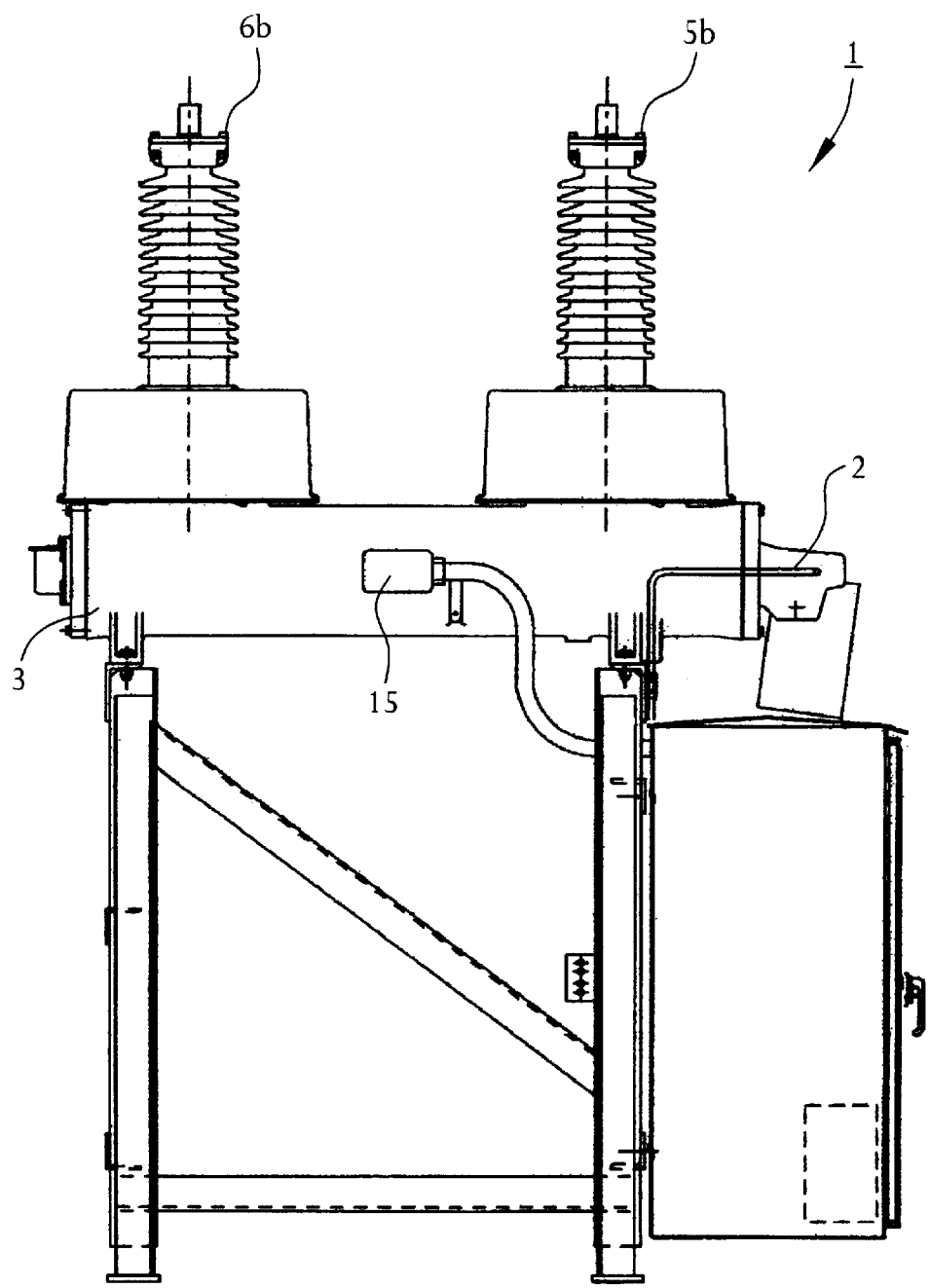
FIG. 1B is a side view of the multiple tank high voltage circuit breaker of FIG. 1A taken along the line C—C of FIG. 1A.
Figure 2:
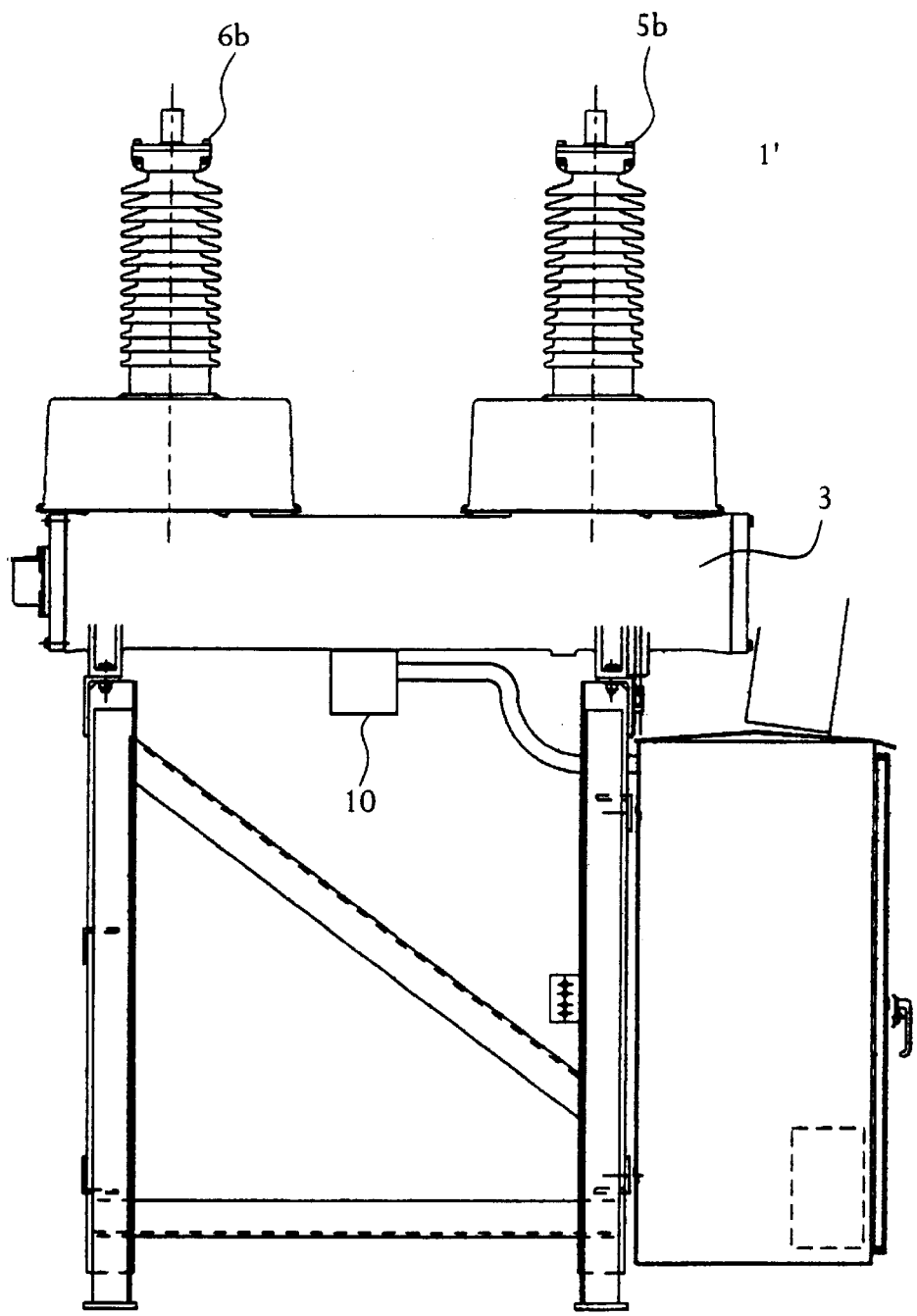
FIG. 2 is a side view of a multiple tank high voltage circuit breaker incorporating a gas density monitoring assembly in accordance with the present invention.

FIG. 2, illustrates a circuit breaker assembly employing the gas density monitoring system of the present invention. As shown therein, a circuit breaker assembly 1' includes three cylindrical tanks 3 (only one tank is visible in the drawing). Each of the three cylindrical tanks 3 is preferably filled with an inert, electrically insulating gas such as $SF_6$. Each tank 3 houses an interrupter (not shown). The interrupters are provided with terminals which are connected to respective spaced bushing insulators. The bushing insulators are shown as bushing insulators 5a and 6a.

In accordance with the present invention, a density monitoring apparatus 10 is coupled to each tank 3. The density monitoring apparatus measures the density of the inert gas directly at the tank and sends an electronic signal indicative of density back to a central control cabinet 9. Because each density monitoring apparatus 10 measures a tank's gas density directly, the network of gas carrying pipes is eliminated. Moreover, each tank can be separately monitored for low gas density levels.

Figure 3:
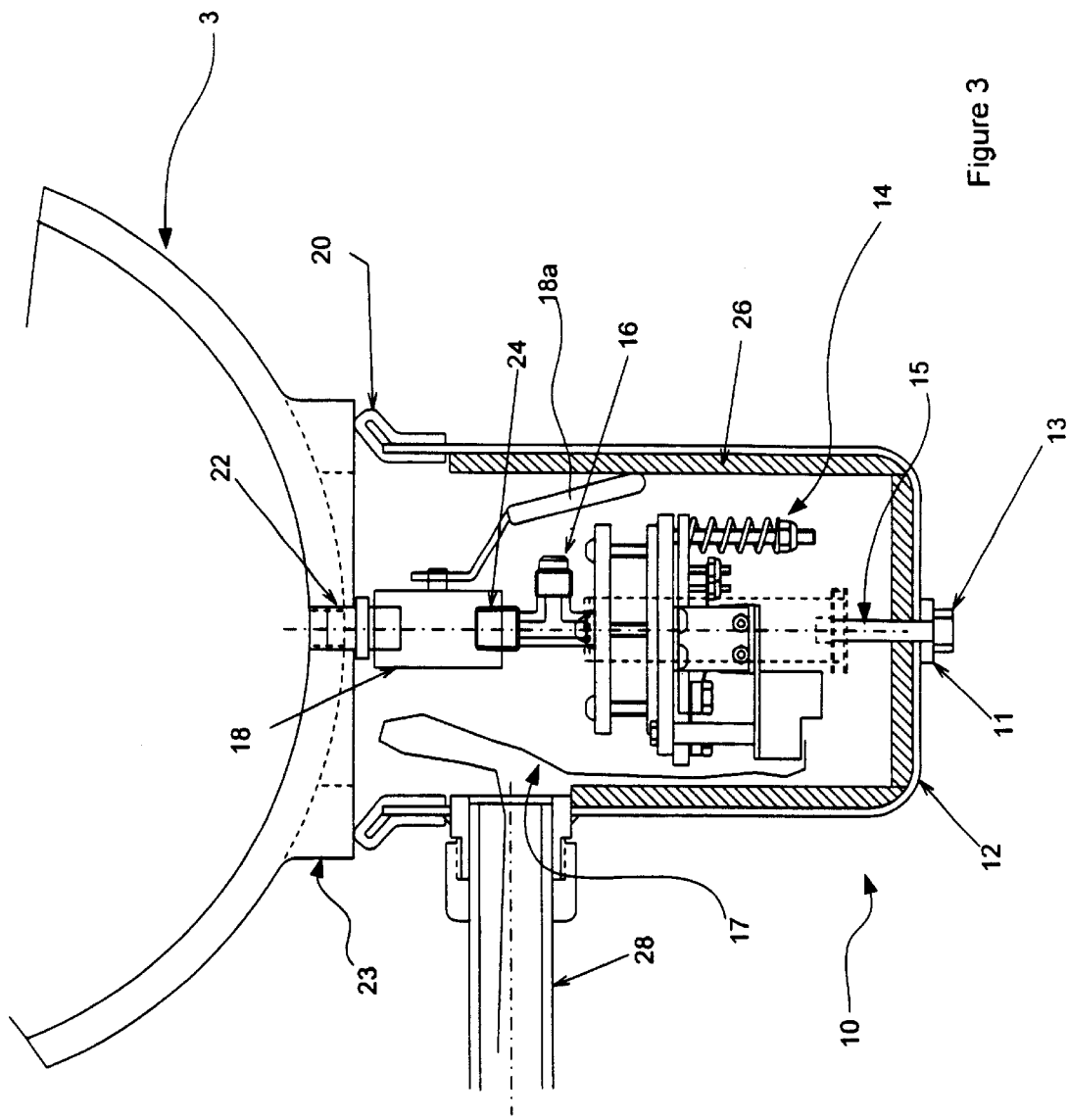
FIG. 3 is a cut-away side view of the gas density monitoring assembly connected to a tank that illustrates the interior components of the assembly.
Figure 4:
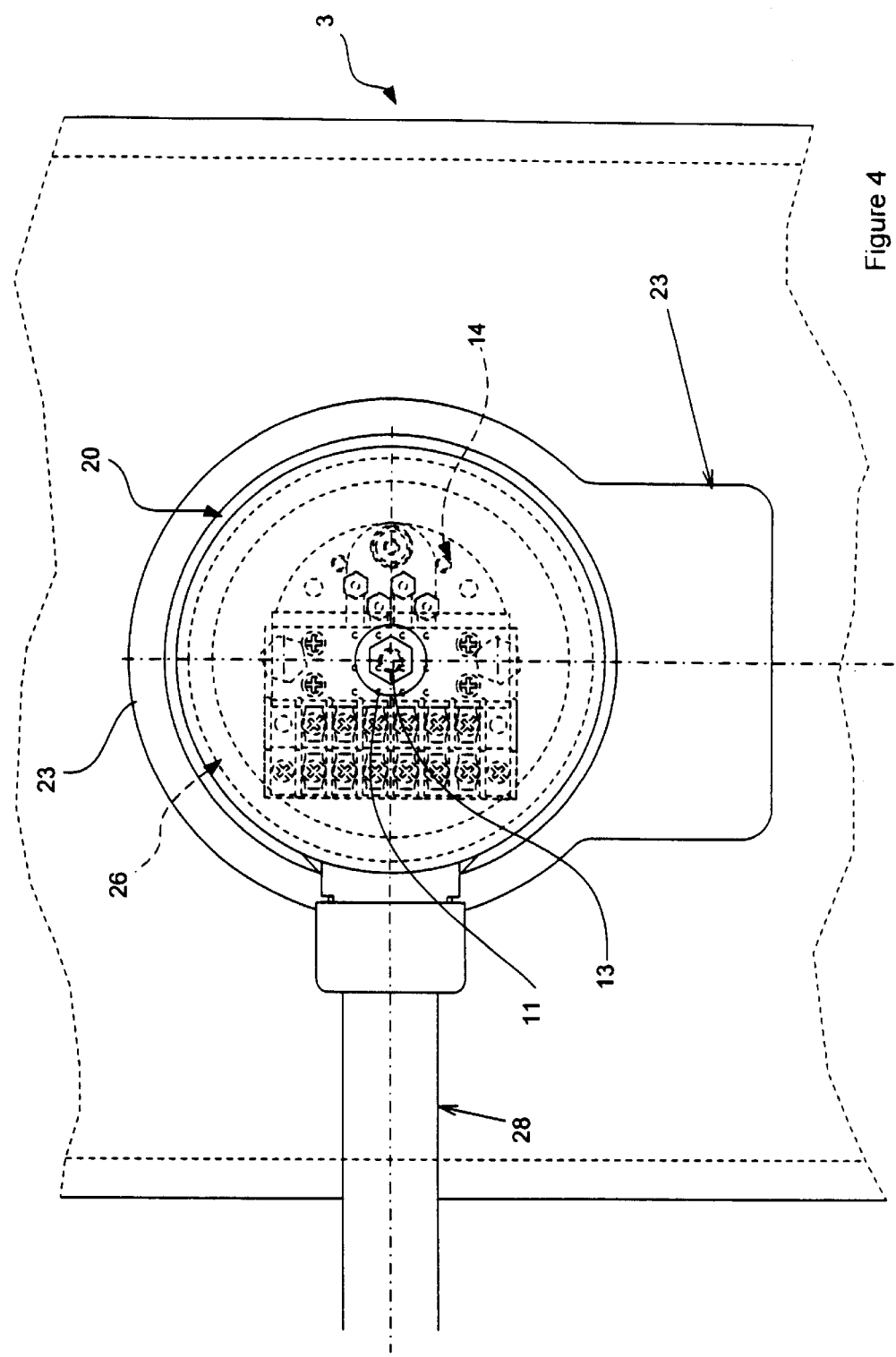
FIG. 4 is a bottom view of the gas density monitoring assembly connected to a tank.

FIGS. 3 and 4 further illustrate aspects of the gas density apparatus in accordance with the present invention. FIG. 3 is a cross-sectional illustration of a gas density monitor apparatus 10 of the present invention. Gas density monitor apparatus 10 comprises a density monitoring device 14 that measures gas pressure and/or tank temperature. Density monitoring device 14 is coupled to tank 3 and is in fluidic communication with tank 3 by way of nipple 22. Preferably, a gas shut-off valve 18, preferably a ball valve, is disposed between density monitoring device 14 and nipple 22. Preferably, a density monitoring device test valve 16 is provided to allow the density measuring characteristics of density monitoring device 14 to be tested and/or calibrated. Preferably, test valve 16 comprises a shraeder valve.

According to an aspect of the invention, density monitoring device 14 is housed within a cover 12. The cover 12 preferably comprises aluminum and is lined with an insulative liner 26. Preferably, liner 26 comprises ¼ inch polyethylene foam insulation. A U-shaped (cross-section) gasket 20 is disposed between cover 12 and tank 3. Preferably, U-shaped gasket 20 is attached to cover 12 with standard super glue. Cover 12 is attached to density monitor device 14 by way of bolt 15 and washer 11. Accordingly, cover 12 is attached to the tank by way of the density monitoring device 14.

A conduit 28 is coupled to cover 12 and provides a passage for electrical wires 17 to provide electrical signals from density monitoring device 14 back to an electrical control panel. Electrical wires 17 connect to density monitoring device 14 by way of terminal block 14b (see FIGS. 5–7).

According to an aspect of the present invention, shut-off valve 18 further comprises valve handle 18a. Handle 18a is rotatable between an open position, wherein gas is permitted to flow through valve 18, and a closed position, wherein gas is prevented from flowing through valve 18. In the open position, valve handle 18a is aligned generally parallel to the flow axis through valve 18 (it is shown in the open position in FIG. 3). In the closed position, valve handle 18a is aligned generally perpendicular to the direction of gas flow through valve 18. Valve handle 18a is sized of a length such that cover 12 can only cover density monitoring device 14 when handle 18a is aligned in the open position. As a result, the density monitoring apparatus cannot be completely assembled to the tank 3 unless gas is flowing through valve 18 toward gas density monitoring device 14. This ensures that density monitoring device 14 is properly monitoring tank pressure when the cover is on.

According to another aspect of the present invention, a shraeder valve is provided between the shutoff (e.g., ball) valve 18 and density monitoring device 14. This allows the density monitoring device to be periodically tested. Such a test would be performed by removing cover 12 and closing shut-off valve 18. Thereafter, gas of a predetermined pressure (as a proxy for density) can be applied to density monitoring device 14 and the output of density monitoring device 14 compared to a benchmark value.

Figure 8:
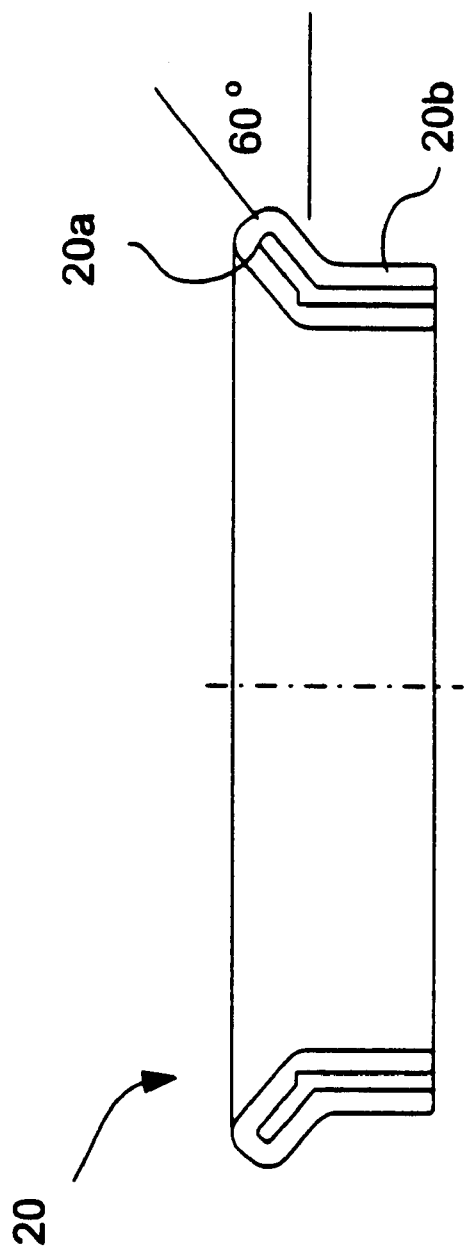
FIG. 8 illustrates a cut-away side view of a gasket employed in connection with the gas density monitoring assembly.

According to another aspect of the invention, U-shaped gasket 20 is attached to the rim of cover 14. FIG. 8 illustrates a cross-sectional side view of gasket 20 of the invention. As shown, gasket 20 comprise an upstanding portion 20b and an angled portion 20a. Angled portion 20a forms and angle of approximately 60 degrees. Preferably, the gasket is formed of a soft vinyl. As a result of the combination of the material (e.g., soft vinyl) and the selected angle (e.g., angle of 20a), the gasket forms a stable, high friction base and seal for cover 12 as it is pressed against the raised boss 23 formed into tank 3.

Stability is provided to the whole assembly 10 by the combination of the cover 12 pressing against the boss 23 and the attachment of the density monitoring device 14 to tank 3 by way of valves 16, 18 and to cover 12 by way of bolt 13.

Density monitoring device 14 is best shown in FIGS. 5–7. As shown density monitoring device 16 is coupled to shraeder valve 16 (which is capped with cap 16a). The shraeder valve 16 is preferably fixedly attached to density monitoring device 14. Density monitoring device 14 also comprises a terminal block 14b that comprises a set of terminals to which signal leads (e.g., leads 17 shown in FIG. 3) can be attached to carry electrical information to a control panel (not shown). Density monitoring device 14 may output, for example, temperature and pressure information from which the gas density can be calculated. Alternatively, the density monitoring device could output density levels (e.g., discrete switch closure signals indicative of discrete density levels). A rigid support member 14a wraps around density monitoring device 14 so that cover 12 can be attached to the density monitoring device and thereby pressed firmly against tank 3. FIG. 6 best illustrates a screw hole 14c whereby bolt 13 attaches cover 12 to support member 14a.

As noted, $SF_6$ gas density can computed by measuring gas pressure and tank temperature. The temperature input comes from a resistive temperature device (RTD) mounted within cover 12. Insulative liner 26 insures that the temperature within cover 12 remains a good proxy for tank temperature. Pressure signals originate in a strain gage transducer mounted on a circuit board within density monitoring device 14. State equations are used to determine gas density, displayed as temperature-corrected pressure for insulating gas. Alarms can be set up for low density or high rate of pressure loss.

Alternatively, the gas density can be determined by using a mechanical device that directly converts temperature and pressure to a density level. Such devices employ a series of switches that output discrete levels indicative of density level. For example, when the density level is at a satisfactory level, the gas pressure causes a first set of electromechanical contacts to close. As the gas pressure, changes to a second discrete level a second set of contact would close indicative of the second level and so on. Alarms can be set for a particular contact set.

In an exemplary tank measuring system, gas density—$SF_6$ gas temperature and pressure are measured and temperature-corrected gas pressure is computed periodically, e.g., every second. These periodic samples are combined to obtain an hourly average corrected gas pressure. If the corrected pressure is less than the caution alarm setting but greater than the danger alarm setting, the caution alarm is logged and activated. If the corrected pressure is less than the danger alarm setting, the danger alarm is logged and activated and the caution alarm is not. This alarm is cleared when the conditions causing the alarm are corrected. This could include resetting the alarm levels or correcting the gas density problem.

While the invention has been described and illustrated with reference to specific embodiments, those skilled in the art will recognize that modification and variations may be made without departing from the principles of the invention as described above and set forth in the following claims.

We claim:

1. An assembly for monitoring the fluidic contents of a tank, comprising:

a monitor device in fluidic communication with the contents of the tank, said monitor device being fixedly coupled at one end to an outside wall of said tank;

an electrical circuit in communication with the monitor device for converting the fluidic communications to electrical representations; and a monitor device cover disposed over said monitor device and said electrical circuit and against an outside wall of said tank.

2. The assembly as recited in claim 1 wherein said monitor device cover is fixed to said tank by way of said monitor device.

3. The assembly as recited in claim 1 further comprising an insulator attached to an inside surface of said monitor device cover to maintain a temperature within said cover in relation to a temperature of said tank.

4. The assembly as recited in claim 1 further comprising a valve disposed between said monitor device and said tank.

5. The assembly as recited in claim 4 wherein said valve comprises at least one of a ball valve and a shraeder type valve.

6. The assembly as recited in claim 5 wherein said valve comprises a ball valve and wherein said ball valve comprises a handle of a preselected length, said length being selected such that said handle must be turned to an open valve position when said monitor cover is disposed over said monitor device.

7. The assembly as recited in claim 1 comprising a gasket disposed between said cover and said vessel.

8. The assembly as recited in claim 7 wherein said gasket comprises a low temperature vinyl.

9. The assembly as recited in claim 1 wherein said monitor device comprises a density monitor.

10. The assembly as recited in claim 9 wherein said density monitor comprises one of a pressure monitor and temperature monitor.

11. An assembly for monitoring the density of gas within a electrical switch containment tank, comprising:

a density monitoring device in fluidic communication with the gas within the tank, said density monitoring device being fixedly coupled at one end to an outside wall of the containment tank;

a monitor device cover having a top, side walls, and a rimmed open bottom, the cover being disposed over said density monitoring device; and a gasket disposed between the cover rim and against the outside all of the tank.

12. The assembly as recited in claim 11 wherein said gas comprises $SF_6$.

13. The assembly as recited in claim 11 wherein the monitor device cover is substantially cylindrical in shape.

14. The assembly as recited in claim 11 further comprising a shut-off valve coupled between the fluidic flow of said tank to the monitor device.

15. The assembly as recited in claim 14 wherein said valve comprises a handle having a length such that the cover can only be placed over said monitoring device when the handle is moved to an open position.

16. The assembly as recited in claim 15 wherein said shut-off valve comprises a ball valve.

17. The assembly as recited in claim 14 further comprising a test point valve providing access to the flow of gas to said monitoring device.

18. The assembly as recited in claim 17 wherein said test point valve comprises a shraeder type valve.

19. The assembly as recited in claim 11 wherein said monitoring device comprises a pressure sensor.

20. The assembly as recited in claim 19 wherein said pressure sensor is a strain gauge.

* * * * *

UNITED STATES PATENT AND TRADEMARK OFFICE
CERTIFICATE OF CORRECTION

| | | |
|---|---|---|
| PATENT NO. | : 6,263,914 B1 | Page 1 of 1 |
| APPLICATION NO. | : 09/288678 | |
| DATED | : July 24, 2001 | |
| INVENTOR(S) | : Jeffry R. Meyer et al. | |

It is certified that error appears in the above-identified patent and that said Letters Patent is hereby corrected as shown below:

Column 2, line 18, delete the word "be";

Column 2, line 22, delete "design" and insert --designed-- therefor;

Column 2, line 47, delete the second occurrence of "a" and insert --an-- therefor;

Column 2, line 48, delete "a" and insert --an-- therefor;

Column 3, line 15, delete "monitor" and insert --monitors-- therefor;

Column 4, line 62, delete "and" and insert --an-- therefor;

Column 5, line 24, insert --be-- after the word "can";

Column 5, line 40, delete "electromechanical" and insert --electro-mechanical-- therefor;

Column 5, line 41, delete "," after the word "pressure";

Column 5, line 42, insert --,-- after the word "level";

Column 6, line 35, delete "a" and insert --an-- therefor.

Signed and Sealed this

Ninth Day of January, 2007

JON W. DUDAS
*Director of the United States Patent and Trademark Office*